United States Patent [19]
Suzuki et al.

[11] Patent Number: 5,723,793
[45] Date of Patent: Mar. 3, 1998

[54] METHODS AND APPARATUS FOR MEASURING STRESS AND STRAIN CHARACTERISTICS OF MICROSCOPIC SPECIMENS

[75] Inventors: Yoshihiko Suzuki, Funabashi; Takashi Kawahito, Fujsawa, both of Japan

[73] Assignee: Nikon Corporation, Tokyo, Japan

[21] Appl. No.: 783,043

[22] Filed: Jan. 15, 1997

[30] Foreign Application Priority Data

Jan. 22, 1996 [JP] Japan ................................. 8-008309

[51] Int. Cl.$^6$ ........................... G01D 1/16; G01D 7/02
[52] U.S. Cl. ................................................ 73/789; 73/791
[58] Field of Search .......................... 73/774, 781, 787, 73/789, 790, 791, 800; 364/508

[56] References Cited

U.S. PATENT DOCUMENTS

| 4,959,552 | 9/1990 | Saffert et al. | 250/560 |
|---|---|---|---|
| 5,495,771 | 3/1996 | Sumi et al. | 73/789 |

Primary Examiner—Richard Chilcot
Assistant Examiner—Max H. Noori
Attorney, Agent, or Firm—Klarquist Sparkman Campbell Leigh & Whinston, LLP

[57] ABSTRACT

Methods and apparatus are disclosed for measuring stress and strain of microscopic specimens under a microscope. The measurements of strain can be performed simultaneously with measurement of the stress, thereby avoiding problems with creep. The apparatus and methods employ an electrically driven microgripper having at least one finger adapted to contact the specimen. The apparatus and methods also employ a device operable to measure the dimensional change (strain) experienced by the specimen upon application of a stress to the specimen using the finger(s) of the microgripper. From measurements of electrical energy supplied to the microgripper before and during application of the stress to the specimen, and of the stress-caused dimensional change of the specimen, stress-versus-strain information about the specimen can be calculated.

20 Claims, 5 Drawing Sheets

METHODS AND APPARATUS FOR MEASURING STRESS AND STRAIN CHARACTERISTICS OF MICROSCOPIC SPECIMENS

FIELD OF THE INVENTION

This invention pertains to methods and apparatus for measuring mechanically induced deformations in shape or profile of microscopic specimens.

BACKGROUND OF THE INVENTION

In recent years with the ongoing development of technology for microscopic observations of minute specimens, it has become possible with respect to such specimens to measure strain (changes in shape and/or dimension) that occur from application of mechanical stress to the specimen.

Representative microscopic specimens that can be the subjects of such measurements include primitive life forms, egg cells (ova) and other biological structures; and microscopic mechanical parts such as directional beams, bi-directional beams, springs, and many other structures.

Figure 4:
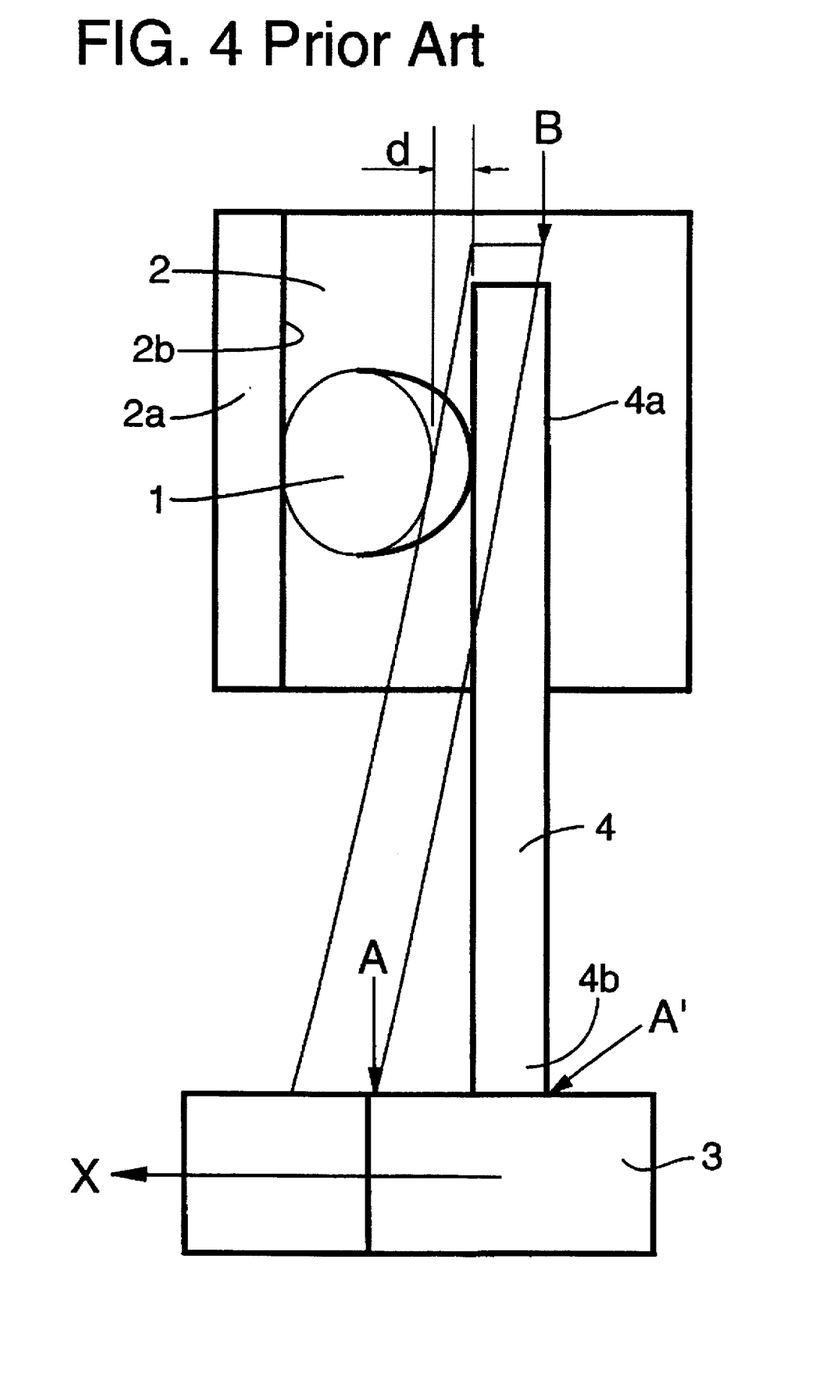
FIG. 4 is a schematic diagram showing certain aspects of an apparatus according to the prior art for measuring mechanical-shape-variation characteristics of microscopic specimens.

FIG. 4 depicts a representative prior art apparatus for measuring strain as experienced by a microscopic specimen when placed under mechanical stress. As the specimen is stressed, the deformation of the specimen can be quantified. The specimen 1, such as an egg cell (ovum), is placed on a support 2 against a surface 2b of an upright 2a. The specimen 1 is contacted by a distal terminus 4a of the glass rod 4. The proximal end 4b of the glass rod is attached to a slide 3 movable in the X dimension (arrow). To urge the distal end 4a against the specimen 1, the slide 3 is moved to the left in FIG. 4.

As the specimen 1 is thus stressed, any resulting strain is observed using a microscope (not shown in FIG. 4). Normally, the Specimen is placed in the center of the field of view of the microscope. Within a certain range, the more distance the slide 3 moves to the left, the greater the force applied to the specimen 1 tending to strain the specimen. Within a certain stress range, the greater the applied force against the specimen, the more strain experienced by the specimen. Depending upon, inter alia, the specimen and the magnitude and direction of the force applied to the specimen, the strain can be elastic or plastic.

A representative length of the glass rod 4 is 50 mm. The proximal end 4b, which is about 1 mm in diameter, is attached to the slide 3. The distal end 4a is about 50 µm in diameter, typically formed by heating and stretching the glass rod at about mid-length. The spring constant of each glass rod 4 must be determined before use by affixing a known small (typically microscopic) mass to the distal end 4a and measuring the amount of flex of the distal end due to the attached mass.

Moving the slide 3 in the X direction as shown causes the distal end 4a to press against the specimen 1. If the force with which the distal end 4a presses against the specimen 1 is sufficiently great, the specimen will experience a measurable strain. For example, after such movement of the slide 3, the point A' moves to the point A and the specimen experiences a decrease "d" in dimension in the X direction. The magnitude of d is measured using a suitable scale in a microscope (e.g., a calibrated reticle). Similarly, the flex (A'—A) of the rod 4 is measured using a microscope.

The measurements of d and (A'–A) are used, together with the measured spring constant of the glass rod 4 and the calculated force applied by the distal end 4a to the specimen 1, to calculate certain mechanical properties of the specimen 1.

With the conventional methods and apparatus as described above, the glass rod 4 tends to be very long (about 50 mm) relative to the diameter of the specimen 1 (e.g., about 100 µm). This makes it extremely difficult or impossible to measure d and (A'–A) using the same scale in the microscope. In addition, many biological specimens have a creep characteristic by which d does not remain constant with a given force applied by the distal end 4a against the specimen. (I.e., such specimens experience a substantial amount of plastic strain.) This causes a problem because, according to the prior art, the instant at which d is measured is not the same instant at which the deflection of the glass rod is measured. As a result, it is difficult to obtain accurate stress-versus-strain data for such specimens.

It is also difficult, using the methods and apparatus according to the prior art, described above, to consistently produce glass rods having the same spring constant and other mechanical characteristics. Each glass rod needs to be individually calibrated before use, which takes time.

SUMMARY OF THE INVENTION

The foregoing shortcomings of the prior art are solved by methods and apparatus according to the present invention. In an apparatus according to the invention, a flexible microgripper is employed to apply a mechanical stress to a microscopic specimen under a microscope. The amount of force applied to the specimen by the microgripper can be very accurately determined.

A key object of the invention is to provide apparatus and methods for making stress-versus-strain measurements of microscopic specimens with ease and accuracy.

Preferred embodiments of an apparatus according to the present invention comprise a microgripper such as disclosed in the Japanese Kokai patent document no. Hei 5-253870 (see Appendix A). Such a microgripper comprises at least one finger that is movable a certain amount upon application of a certain amount of electrical energy (typically voltage) to the finger. The finger(s) are operable to move sufficiently to contact the specimen without stressing the specimen and to move sufficiently relative to the specimen to apply a stress to the specimen. Each such movement is a function of the amount of electrical energy applied to the finger. According to one embodiment, the finger(s) are operable to apply a compressire stress to the specimen. For example, the microgripper can comprise two opposing fingers, wherein the fingers are cooperative to provide the compressire stress to the specimen located between the fingers. According to another embodiment, the finger(s) are operable to apply a tensile stress to the specimen.

Preferred embodiments of an apparatus also comprise a means for determining any strain "d" of the specimen occurring as a result of application of a stress to the specimen using the microgripper, compared to when no stress is being applied to the specimen. According to one embodiment, the means for determining strain comprises a microscope that is operable to produce an enlarged image of the specimen. Such a microscope preferably includes a scale for measuring dimensions of the specimen as viewed in the enlarged image. According to another embodiment, an imaging device is included for capturing the enlarged image, and a display (e.g., CRT, flat-panel display) is included for displaying the captured image.

Preferred embodiments of an apparatus also comprise a means for measuring the amount of electrical energy $V_0$ applied to each finger before applying the stress to the specimen and the amount of electrical energy $V_F$ applied to each finger during application of the stress to the specimen.

Finally, preferred embodiments of an apparatus also comprise means for calculating, from the $V_O$, $V_F$, and d values, a stress-versus-strain characteristic of the specimen.

Further with respect to the microgripper, certain embodiments comprise a finger that is operable to reflect light. In such embodiments, the means for measuring strain includes a light projector, a light sensor, and a calculating means (such as a computer or processor). The light projector is operable to project a beam of light (e.g., a laser beam or beam from an LED) and cause the beam to be incident on the finger in a manner by which the light reflects from the finger. The light sensor is situated relative to the finger so as to receive light reflected from the finger, and is operable to sense changes in trajectory of the reflected light as a function of finger position. The calculating means is operable to calculate, from a change in finger position as sensed by the light sensor after applying stress to the specimen (compared with before applying the stress, a value of "d".

According to certain embodiments, the means for measuring strain of the specimen comprises a microscope operable to produce an enlarged optical image of the specimen. Also included is a means for processing the screen image obtained while applying a stress to the specimen compared to the screen image obtained before applying the stress to the specimen, so as to obtain an amount of dimensional change experienced by the specimen while a stress is being applied compared to before the stress was applied. The means for processing the screen image preferably comprises means for converting the screen image into pixels. In such an embodiment, the amount of dimensional change experienced by the specimen while a stress is being applied compared to before the stress was applied is determined based upon a change in the illumination status of the pixels.

Preferred embodiments of an apparatus according to the invention also comprise a microscope (preferably inverted) and a microscope stage. The stage is operable to move the specimen to a position adjacent the finger of the microgripper prior to application of a stress to the specimen. Such embodiments also preferably comprise a manipulator for moving the microgripper relative to the specimen.

The present invention also encompasses methods for measuring a stress-versus-strain characteristic of a microscopic specimen. Such methods preferably comprise the following steps. First, a specimen is disposed relative to a finger of a microgripper. The microgripper is operable to move the finger a distance corresponding to the amount of electrical energy (e.g., voltage) supplied to the microgripper. When the finger is contacting the specimen but not applying a stress to the specimen, the amount of electrical energy $V_O$ supplied to the microgripper is measured. The amount of electrical energy is then increased to $V_F$ (which is also measured) to urge the finger to move relative to the specimen and apply a stress to the specimen. Any dimensional change imparted to the specimen as a result of the stress is also measured. Preferably, a measure of the amount of stress (i.e., a measurement of the force) applied to the specimen is calculated.

The foregoing and additional features and advantages of the present invention will be more readily apparent from the following detailed description, which proceeds with reference to the accompanying drawings.

DETAILED DESCRIPTION

Apparatus according to the present invention comprise a "microgripper" having at least one "finger." A microgripper functions as a microscopic forceps, wherein the movement and positioning of each "finger" can be precisely controlled. A suitable microgripper, by way of example, for use in apparatus and methods according to the invention is disclosed in Japanese Kokai patent document no. Hei 5-253870 (see Appendix A). Such a microgripper comprises at least one "finger" having a position and gripping force that can be changed by application of electrical energy to the microgripper, e.g., electrical voltage. Examples of means for controllably moving the finger include a static electric force, an electromagnetic force, a thermal bimetal, a thermal bimorph, or an electrostrictive element.

First Preferred Apparatus Embodiment

Figure 1:
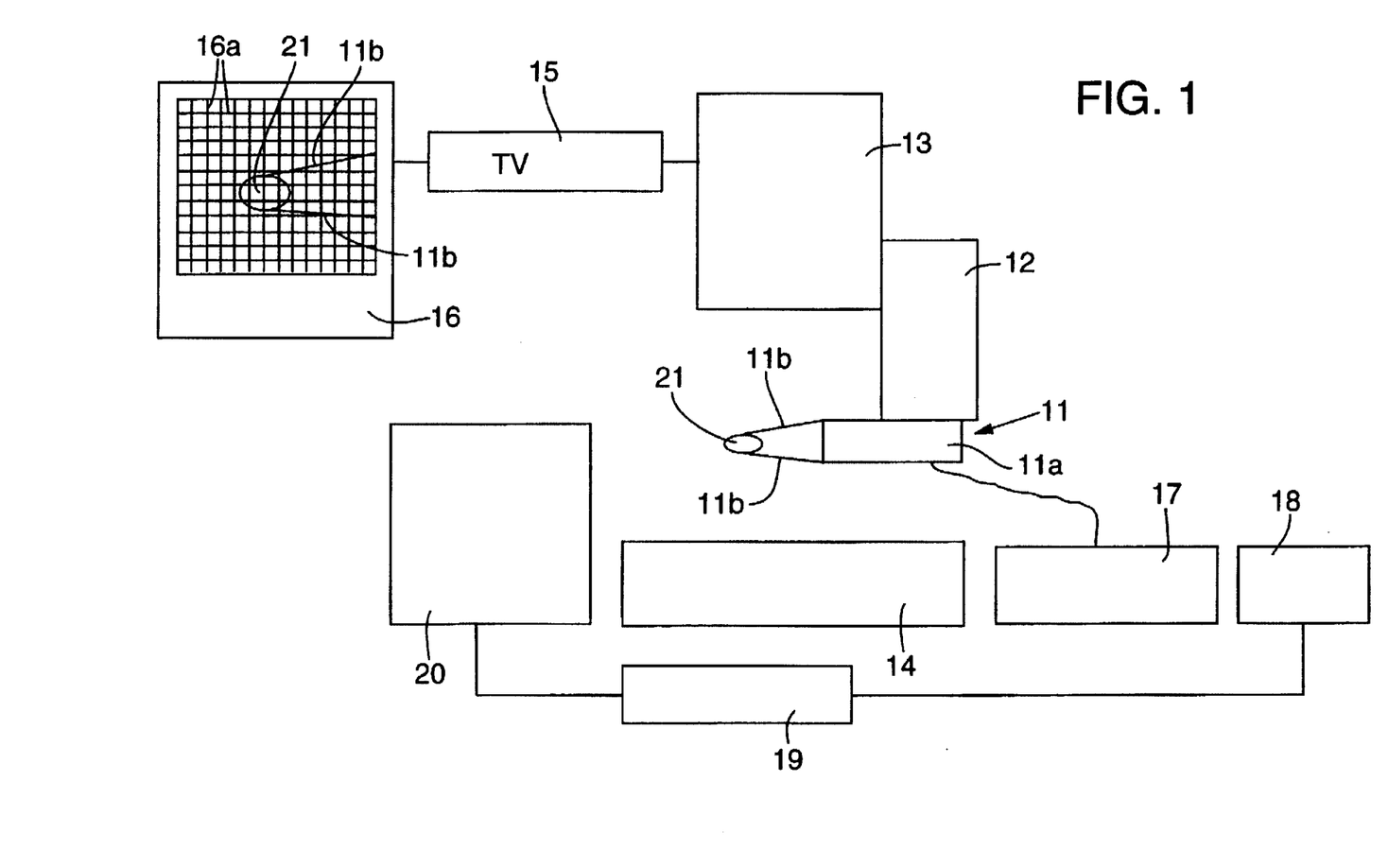
FIG. 1 is a block diagram of a first preferred embodiment of an apparatus according to the invention.

An exemplary microgripper 11 useful in the first preferred embodiment is shown in FIG. 1. The microgripper 11 comprises opposing fingers 11b mounted to a support 11a. The support 11a is made of silicon (Si) and the fingers 11b are made of silicon nitride membrane extending from the support. Further details about the microgripper 11 and how it is made are disclosed in the JP Kokai patent document no. Hei 5-253870 cited above. The microgripper 11 preferably operates using two drive schemes: a thermal bimorph drive (finger motion generated when voltage is applied to a separate microcoil on each finger) and a drive employing the Lorentz force generated through interaction with an external magnetic field.

Figure 5:
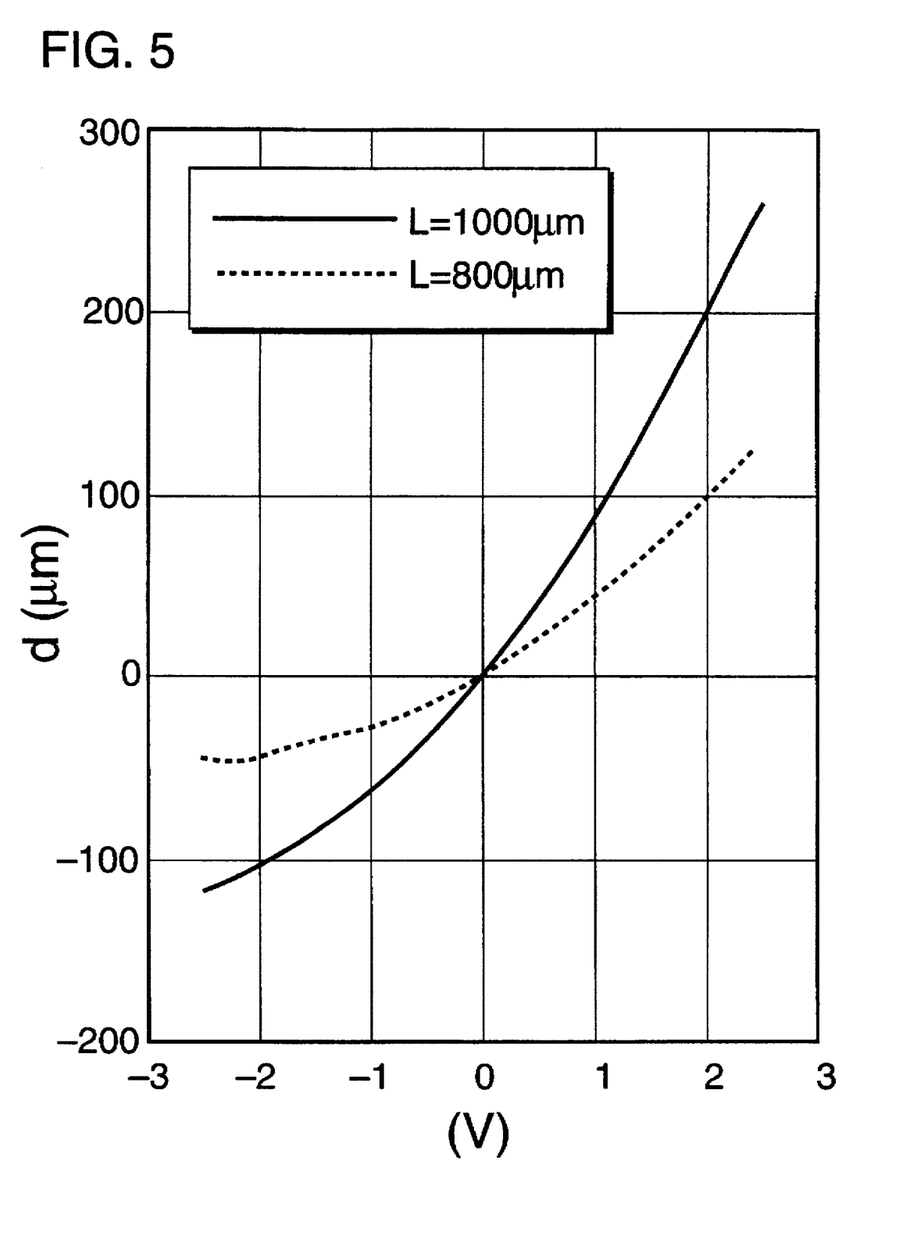
FIG. 5 is a plot showing the relationship between drive voltage of a microgripper as used in any of the embodiments of FIGS. 1–3 and the corresponding amount by which the microgripper finger(s) are flexed.

FIG. 5 shows a graph of the drive characteristics of the microgripper 11 in an aqueous solution obtained in experiments performed by the inventor and disclosed in the Japanese Kokai patent document no. Hei 5-253870 cited above. Data with respect to two types of microgrippers are shown with finger lengths of 1000 μm and 800 μm, respectively, manufactured using a micromachining method. The horizontal axis is the drive voltage applied to the microgripper and the vertical axis is the resulting flex of each of the fingers upon application of the drive voltage.

Further with respect to FIG. 5, the flex d of a microgripper finger can be calculated as follows:

$$d = k_B(V_F^2/R) + k_L(V_F/R) \tag{1}$$

wherein $k_B$ is the bimorph drive coefficient, $k_L$ is the Lorentz force coefficient, $V_F$ is the applied voltage, and R is the resistance of the respective microcoil.

The force $F_g$ applied to a microscopic specimen by a finger of a microgripper can be calculated according to the following Equation (2) from known values of the applied voltage $V_O$ to the microgripper when the specimen is in contact with at least one finger but the finger is causing no deformation of the specimen, the applied voltage $V_F$ when the specimen has been deformed a certain amount by the finger(s) pressing against the specimen, the spring constant $k_s$ of the microgripper finger, and the amount of strain "d" experienced by the specimen:

$$F_g=k_s[(k_B/R)V_F^2+(k_L/R)V_F-(k_B/R)V_0^2-(k_L/R)V_0]-k_z \cdot d$$

Referring further to FIG. 1, the microgripper 11 is preferably mounted to a manipulator 12 (preferably hydraulically driven) situated on a stage 14 of a microscope 13 (preferably an inverted microscope). The microscope 13 provides an optically enlarged image of the specimen and of the finger(s) of the microgripper. The microscope 13 preferably comprises a monitor 16 connected to a closed-circuit television camera 15 or analogous image-capturing device, wherein the monitor 16 provides a display of the image captured by the camera 15. The image displayed on the monitor preferably includes a scale 16a provided, e.g., as a reticle scale in the microscope. The scale can be used for measuring the strain of the specimen (e.g., the "d" dimension) in response to stress applied to the specimen by the microgripper. Because the scale 16a is used only for measuring the strain of the specimen, the need in the prior art to change measurement scales is eliminated. This substantially reduces the time required to perform a stress-versus-strain measurement. Also, accuracy is increased because strain measurements can be performed simultaneously with applying the stress to the specimen.

According to this embodiment, a master input device 17 is connected to an electrical pole of the microgripper 11. The master input device includes inter alia, controls enabling the user to cause movement of the finger(s) of the microgripper. For example, the master input device 17 preferably comprises a potentiometer (not shown) operable for adjusting the voltage applied to the microgripper for moving the finger(s). The master input device 17 is connected to a drive power supply 18. The drive power supply 18 is connected to a computer 20 via an analog-to-digital (A/D) converter 19. The computer 20 is programmed with software by which the pressing force of the finger(s) 11b against the specimen is calculated from $V_0$, $F_F$, and d, preferably using Equation (2).

First Preferred Method Embodiment

According to a preferred embodiment of a method according to the present invention, the fingers of a microgripper such as that in FIG. 1 are disposed adjacent or in contact with a microscopic specimen without deforming the specimen. The voltage (or other suitable measure of electrical energy) applied to the microgripper in order for the fingers to contact the specimen without deforming the specimen is measured. This initial voltage is $V_0$.

The specimen is then pressed between the fingers with sufficient force to cause a measurable deformation of the specimen (usually without destroying the specimen). The increased force applied by the fingers is achieved by increasing the voltage (or other suitable electrical energy input) to the microgripper. The increased electrical energy $V_F$ is measured. The resulting strain (amount of dimensional deformation) of the specimen is also measured and compared to the shape of the specimen at $V_0$ to obtain a value of d.

Using equation (2), above, the gripping force $F_g$ can be calculated (by the computer 20) using the values of variables as determined above. From the relationship between the stressing force $F_g$ and the strain d for a population of specimens, quantitative information concerning how and to what extent the specimen responds to application of the mechanical stress can be obtained.

$V_0$ and $V_F$ are preferably automatically input to the computer. The strain of the specimen can be readily measured using the monitor 16 and scale 16a, and the measurements can be input by the operator into the computer using a keyboard or other suitable data-entry device. Thus, the stress-versus-strain characteristics of any of various specimens can be rapidly, simply and accurately measured. Furthermore, since the strain of the specimen can be readily observed and quantified using the scale 16a on the monitor 16, there is no need to change scales. Thus, strain measurements can be performed simultaneously with application of stress using the microgripper. This avoids problems with creep and related phenomena that could otherwise lead to erroneous results.

Furthermore, the image of the specimen magnified by the microscope 13 and displayed on the monitor 16 permits multiple individuals to simultaneously observe the specimen.

Second Preferred Apparatus Embodiment

Figure 2:
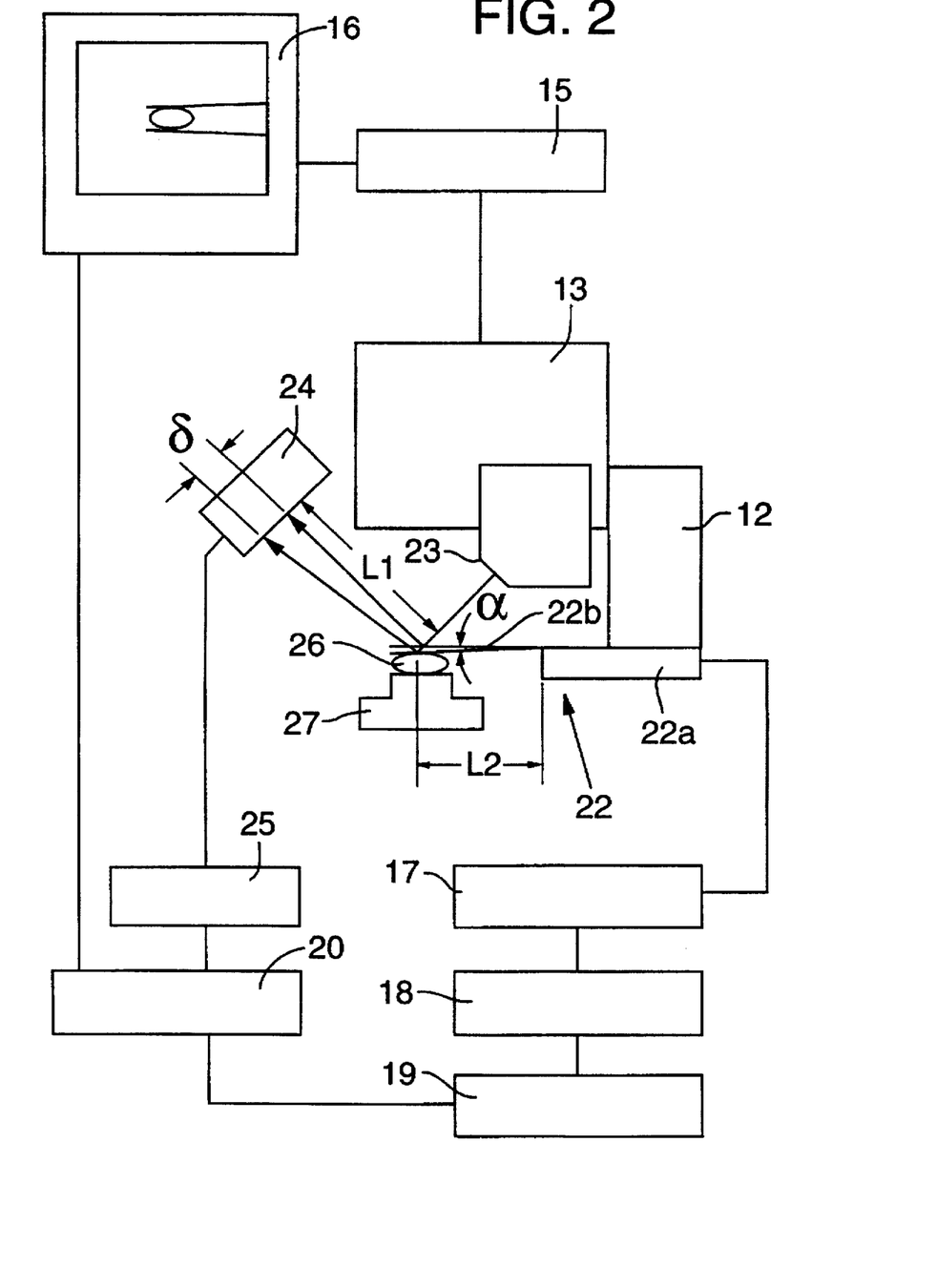
FIG. 2 is a block diagram of a second preferred embodiment of an apparatus according to the invention.

This embodiment, having utility for measuring stress-versus-strain characteristics of microscopic specimens, is depicted in FIG. 2, in which components that are the same as in FIG. 1 have the same reference designators. This embodiment comprises, instead of a microgripper having two fingers as in the FIG.-1 embodiment, a microgripper 22 having only one finger 22b attached to a microscope stage 22a. The finger 22b is adapted to press against a specimen 26 placed on a support 27 serving as a stationary object.

The FIG.-2 embodiment also preferably comprises a light projector 23 (e.g., a suitable laser) operable to project a beam of light onto the finger 22b, and a light sensor 24 operable to detect light reflected from the finger 22b. Electrical signals from the light sensor 24 are converted to digital signals by an A/D converter 25 and routed to the computer 20.

Supplying sufficient voltage (or other suitable form of electrical energy) to the microgripper 22 causes the finger 22b to be urged against the specimen 26. Meanwhile, the light projector 23 directs a beam of light to reflect from the finger 22b to the sensor 24. As the finger moves in response to application of electrical energy to the microgripper, the trajectory of light reflecting from the finger 22b changes. These changes in trajectory are sensed by the light sensor 24 and input to the computer 20 which calculates the amount of movement of the finger 22b. Thus, this embodiment eliminates the scale 16a in the FIG.-1 embodiment and the need to manually measure d.

The following relationship applies with respect to a distance L1 (a predetermined distance from the point of reflection on the surface of the finger 22b to the light-receiving surface of the sensor 24), the displacement of light $\delta$ on the surface of the light sensor 24, and the flex angle $\alpha$ of the finger 22b:

$$\delta/L1=\tan(2\alpha)$$

As can be seen, whenever the finger 22b is moved by the flex angle $\alpha$, the angle at which light reflects from the finger is $2\alpha$. By determining $\delta$, the flex angle $\alpha$ can be readily calculated. Also, if the distance L1 is known in advance, then the flex angle $\alpha$ can be used to calculate the amount of flex of the finger 22b.

Furthermore, the distance L2 from the proximal end of the finger 22b to point at which the light beam is incident on the finger is preferably known beforehand.

This embodiment permits measurements of the stress-versus-strain characteristics of microscopic specimens based on changes in the location of reflected light received by the light sensor 24. The computer 20 is employed to quickly, easily, and accurately calculate the strain experienced by the specimen 26.

FIG. 2 shows the specimen 26 placed relative to the finger 22b in a manner suitable for application by the finger 22b of a compression stress to the specimen 26. It will be appreciated that the finger 22b can also be used to perform evaluations of the tensile strength of a specimen. This is done by moving the specimen to above the finger, affixing one end of the specimen to the finger and an opposing end of the specimen to a fixed support, and moving the finger as described above.

In this embodiment, as indicated above, the light projector 23 is preferably a laser. However, it will be understood that the light projector can also be any of various other suitable sources of light such as, but not limited to, a light-emitting diode (LED).

Second Preferred Method Embodiment

This method embodiment preferably involves use of an apparatus as described above with respect to FIG. 2. A specimen 26 is placed on the stage 27. The specimen 26 and the microgripper 22 are manipulated so as to cause the distal end of the finger 22b to just contact the specimen 26. A voltage is applied to the microgripper 22 by the drive power supply 18. Simultaneously, the voltage is converted to a digital signal by the A/D converter 19 and input to the computer 20 as a "starting" voltage $V_0$. Light (e.g., a laser beam) is directed from the light source 23 so as to be incident on the distal end of the finger 22b. Light reflected from the finger 22b is detected by the light sensor 24; the light sensor 24 senses the location on the sensor surface at which the reflected light is incident. The corresponding signal produced by the sensor 24 is converted to a digital signal by the A/D converter 25 and input to the computer 20.

To apply stress to the specimen 26, an increased voltage is applied by the drive power supply 18 to the microgripper 22; this causes the distal end of the finger 22b to be urged against the specimen 26 sufficiently to apply stress to the specimen. The voltage applied to the microgripper is simultaneously directed to the A/D converter 19 and is input as a digital signal to the computer 20. Further simultaneously, light reflected from the distal end of the finger 22b is detected by the light sensor 24; any changes in the position at which light is incident on the sensor 24 is converted to a digital signal by the A/D converter 25 and input to the computer 20. The flex angle α is calculated by the computer 20, and is used by the computer 20 to calculate the magnitude of motion of the finger 22b.

Third Preferred Apparatus Embodiment

Figure 3:
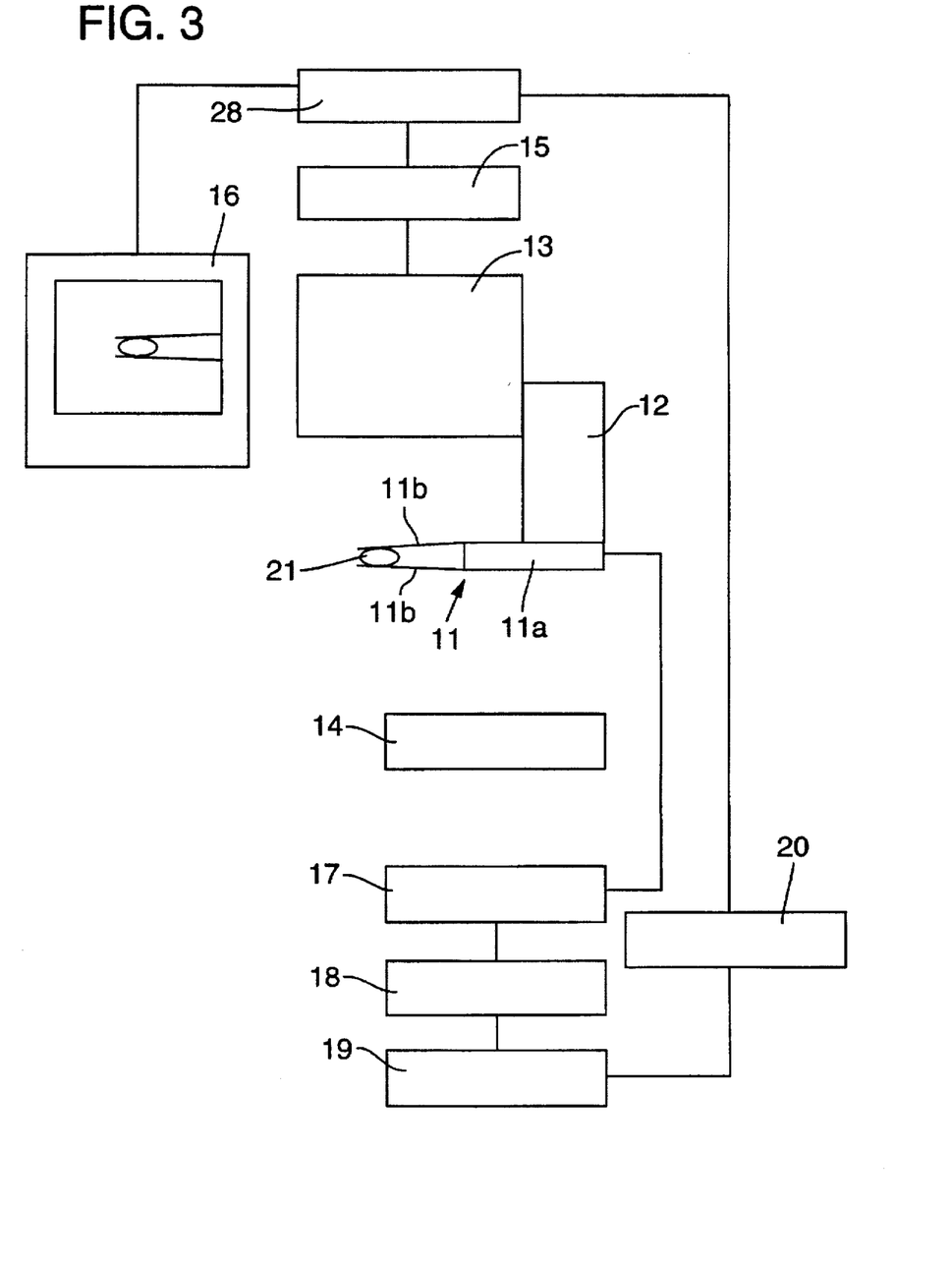
FIG. 3 is a block diagram of a third preferred embodiment of an apparatus according to the invention.

A third preferred apparatus embodiment is shown in FIG. 3. This embodiment shares many features with the FIG.-1 embodiment, and components that are the same as shown in FIG. 1 have the same reference designators and are not described further. In the FIG.-3 embodiment, a closed-circuit TV camera 15 is connected to a screen-image processor 28 to which the computer 20 and the monitor 16 are connected. The TV camera 15 is used to pick up images produced by the microscope 13. The screen-image processor 28 is operable to detect changes in the image and convert the image into pixels; signals from the screen-image processor 28 are conducted to the computer 20 which performs calculations as described above.

EXAMPLE 1

An apparatus similar to that shown in FIG. 1 was used to investigate the stress-versus-strain characteristics of a 100-μm diameter sea-urchin ovum employed as a representative specimen. The specimen, initially substantially spherical, was suspended in sea water in a laboratory dish placed on the stage 14 of the microscope 13. The monitor 16 was used to observe the specimen 21. For measuring shape changes of the specimen, the scale 16a was also displayed on the monitor 16.

Using the master input device 17, the microgripper 11 was manipulated until the specimen 21 was situated between the fingers 11b. The drive voltage required for the microgripper 11 to just hold the specimen (without causing measurable strain of the specimen) was generated by the drive power supply 18, routed to the master input device 17, and then to the microgripper 11. The drive voltage also underwent analog-to-digital conversion via the A/D converter 19 and then input to the computer 20. The initial voltage $V_0$ was 0.65 V.

Using the master input device 17, the voltage applied to the microgripper was increased ($V_F$=1.2 V) so as to deform but not rupture the specimen. The voltage was converted to a digital signal by the A/D converter 19 and input to the computer 20. Meanwhile the profile of the specimen was evaluated on the monitor 16 using the scale 16a; thus, "d" was determined to be approximately 20 μm. This value of d was input into the computer 20 using a keyboard (not shown in FIG. 1). From the $V_0$, $V_F$, and d information stored in the computer 20, the computer 20 calculated the gripping force applied to the specimen by the microgripper, using equation (2), above. In this example, a gripping force of 29.9 nN caused a 20-μm compression of the specimen.

EXAMPLE 2

An apparatus similar to that in FIG. 2 was used in this example to evaluate stress and strain of a sea-urching ovum used as a specimen. The length of the finger 22b was 800 μm and the calculated amount of finger flex was 8 μm. Thus, the amount of deformation of the sample 26 was also 8 μm.

Based on the voltage $V_0$ applied to the microgripper at the start of measurement and the voltage $V_F$ applied to cause an 8-μm compression of the specimen 26, the computer calculated the stress responsible for such strain to be 20 nN.

EXAMPLE 3

An apparatus as shown in FIG. 3 was used in this example. The specimen was a 100-μm diameter sea urchin ovum placed in a laboratory dish filled with sea water. The dish was placed on the stage 14 of the microscope 13.

The specimen 21 was maneuvered to between the fingers 11b of the microgripper 11. While observing the specimen 21 using the microscope 13, the fingers 11b were moved together sufficiently to just contact the specimen 21 without deforming the specimen, and the voltage $V_0$ driving the microgripper was noted ($V_0$=0.65 V). This voltage was instantaneously converted to a digital signal by the A/D converter 19 and input to the computer 20.

The master input device 17 was manipulated so as to apply a greater voltage ($V_F$=1.2 V) to the microgripper 11 which resulted in a measurable strain exhibited by the specimen 21. This increased voltage was instantaneously converted to a digital signal by the A/D converter 19 and input to the computer 20. The resulting strain of the specimen 21 as shown on the monitor 16 was processed by the screen image processor 28 to yield a value of d=30 μm deformation imparted to the specimen 21.

Values of $V_0$, V, and d were used in a calculation, using equation (2), revealing that the 30 μm deformation resulted from application of a 32 nN force to the specimen using the microgripper.

In any of the embodiments discussed above, the voltage required to just contact the specimen with the finger(s) of the microgripper was regarded as $V_0$. It will be understood that $V_0$ can be any suitable "baseline" value, and $V_0$ is not necessarily determined at the instant the finger(s) just contact the specimen.

Also, in any of the embodiments discussed above, the $V_0$ and $V_F$ values were preferably voltage values. However, it will be understood that $V_0$ and $V_F$ can be derived from any other suitable measure of electrical energy applied to the microgripper. In any event, measures of electrical energy can be obtained by any of various ways.

Whereas the invention has been described in connection with preferred embodiments and examples, it will be understood that the invention is not limited to those embodiments and examples. On the contrary, the invention is intended to encompass all alternatives, modifications, and equivalents as may be included within the spirit and scope of the invention as defined by the appended claims.

APPENDIX A (11) JAPANESE PATENT APPLICATION LAID OPEN NO. 5-253870

(43) LAID OPEN DATE: Oct. 5, 1993

(21) application Ser. No. 4-50756

(22) APPLICATION DATE: Mar. 9, 1992

(71) APPLICANT: NIKON CORPORATION (72) INVENTOR: SUZUKI, Yoshihiko (54) TITLE OF THE INVENTION: MICROGRIPPER (57) ABSTRACT

[OBJECT]

To provide a microgripper having a pair of fingers for nipping a microscopic object within a visual field of a microscope, which can achieve a large amount of displacement of the fingers with application of a low voltage.

[STRUCTURE]

A pair of flexible fingers, which are made of inorganic or organic material, extend from one end of a gripper body so as to be opposite to each other with a gap therebetween. One or more coil layers are formed in at least one flexible fingers. The coil layer is made of superconductive material. Protruding or indenting nippers are formed on the tip of the flexible fingers.

[CLAIMS]

1. A microgripper having a gripper body and a pair of flexible fingers extending from one end of the gripper body, the flexible fingers facing each other with a gap therebetween, a coil layer being formed in each of the flexible fingers.

2. The microgripper according to claim 1, wherein a plurality of coil layers are formed in each of the flexible fingers.

3. The microgripper according to claim 1 or 2, wherein the flexible fingers are made of inorganic material.

4. The microgripper according to claim 1 or 2, wherein the flexible fingers are made of organic material.

5. The microgripper according to any of claims 1 through 4, protruding or indenting nippers are formed on the tip of the flexible fingers.

6. The microgripper according to any of claims 1 through 5, wherein the coil layer is made of superconductive material.

[DETAILED DESCRIPTION OF THE INVENTION]

[0001]

[FIELD OF THE INVENTION]

This invention relates to a microgripper for nipping a microscopic object within a visual field of a microscope.

[0002]

[Background of the Related Art]

A microgripper has been conventionally used to nip, for example, a microscopic mechanical component or an organism, such as a cell, within a visual field of a microscope.

[0003] FIG. 11 illustrates a conventional electrostatic microgripper, in which a pair of fingers 13 extend from one end of the gripper body. The fingers 13 face each other with a space therebetween, and fixed electrodes 15 are positioned between the fingers 13.

[0004] If a voltage is applied to the fixed electrodes 15, static electricity is generated between the fixed electrode 15 and the fingers 13, thereby opening and closing the fingers 13.

[0005] FIG. 12 illustrates another conventional microgripper using a piezoelectric element. A base 17, displacement enlarging portions 19, and fingers 21 are monolithically formed from a copper alloy thin plate through chemical etching. A piezoelectric element 23 is positioned within the base 17.

[0006] Expansion and contraction of the piezoelectric element 23 is transmitted to fingers 21 through the displacement enlarging portions 19, whereby the fingers 21 open and close.

[0007] However, these types of microgrippers require a high voltage (from several tens to several hundreds volt) to open and close the fingers 13 or 21 in a relatively wide range.

[0008] Especially, with the electrostatic microgripper shown in FIG. 11, displacement of the fingers 13 is limited to several microns (μm), and an object that is to be handled is extremely limited because the dimensions of the object must fall within the range of the displacement.

[0009] Furthermore, the conventional microgrippers have only a low degree of freedom in displacement of the fingers 13 (and 21). Prior to nipping an object, the position of the microgripper must be adjusted so that the object is positioned in the middle of the two fingers.

[0010] This invention is conceived to overcome these problems in the prior art, and it is an object of the invention to provide a microgripper which is capable of opening and closing its fingers in a wide range with relatively low voltage application.

[0011]

[MEANS FOR ACHIEVING THE OBJECT]

In one aspect of the invention, a microgripper has a gripper body and a pair of flexible fingers on one end of the gripper body. The flexible fingers face each other with a gap therebetween. A coil layer is formed in each of the flexible fingers.

[0012] Two or more coil layers may be formed in each of the flexible fingers. The flexible fingers are made of inorganic material.

[0013] The flexible fingers may be made of organic material. Protruding or indenting nippers are formed on the tip of the flexible fingers for better gripping.

[0014] The coil layer is made of superconductive material.

[0015] If the microgripper is positioned in the magnetic field, and when a voltage is applied to the coil layers of the flexible fingers, then the coil layers receive Lorentz force from the magnetic field, and the flexible fingers bend.

[DESCRIPTION OF PREFERRED EMBODIMENTS]

[0006] FIG. 1 illustrates a microgripper according to an embodiment of the invention. The microgripper has a plate-like gripper body 31.

[0017] A pair of flexible fingers 33 extend from one end of the gripper body 31 so as to be opposite to each other with a gap therebetween. The flexible fingers 33 are formed as long rectangular plates. The flexible fingers 33 and the gripper body 31 are monolithically formed.

[0018] Protruding nippers 35 are formed in the inner surfaces of the respective flexible fingers 33 so as to be opposed to each other on the tip of the flexible fingers 33. A coil layer 37 is formed on the outer surface of each of the flexible fingers 33.

[0019] The coil layer 37 extends along the periphery of the rectangular flexible finger 33 on the outer surface of the flexible finger 33. Both end of the coil layer 37 are connected to the connection layers 39 which are formed on the gripper body 31. The connection layers are connected to the electrode layers 41 which are also formed on the gripper body 31 with a space therebetween.

[0020] FIG. 2 shows an example of a manufacturing process of the microgripper. First of all, a single-crystalline silicon substrate 43 with a thickness of 200 μm and a surface orientation of 100 is prepared as the material to form the gripper body 31 and the flexible fingers 33.

[0021] A silicon nitride film 45 having a thickness of 0.3 μm is formed on either surface of the single-crystalline silicon substrate 43 by vapor deposition so that the entire area of the surface is covered, as shown in FIG. 2(a). A portion of the silicon nitride film 45 is removed through lithography. The single-crystalline silicon substrate 43 is anisotropically etched using KOH solution to form trenches 47.

[0022] The trenches 47 are formed to provide protruding nippers 35 on the tip of the inner surface of the flexible fingers 33 in the later step. The trenches 47 can be shaped into a desirable form according to an object to nip.

[0023] Then, a silicon nitride film 49 is again formed by vapor deposition up to 0.3 μm on the entire area of the previous silicon nitride film 45 on either side of the substrate 43, as shown in FIG. 2(b). The silicon nitride films 49 and 45 are patterned into a rectangular shape define the outline of the flexible fingers 33 through lithography, as shown in FIG. 2(c).

[0024] In the embodiment, the microgripper has long rectangular flexible fingers 33, and therefore, the silicon nitride films 49 and 47 are patterned into a rectangular shape. However, the flexible fingers 33 may have a desirable shape depending on use. The silicon nitride films 49 and 47 can be patterned into, for example, a polygonal shape (such as a trapezoid or triangle), a shape defined by curves (e.g., semicircle), or a shape defined by straight lines and curves. The center portion of the flexible finger 33 may be punched.

[0025] Then, a conductive film 51 is formed so as to cover the entire area of the patterned silicon nitride film 49 and the substrate 43 by, for example, vacuum evaporation or spattering (FIG. 2(d)). Materials of the conductive film 51 include gold, copper, aluminum, etc. The conductive film 51 is patterned to form a coil layer 37, connection layers 39 and electrode layers 41 on either side of the substrate 43 (FIG., 2(e)).

[0026] Next, as shown in FIG. 2(f), an unnecessary portion is removed from the single-crystalline silicon substrate 43 by etching to complete the microgripper shown in FIG. 1.

[0027] The resultant microgripper has flexible fingers 33 with a thickness of 0.6 μm, a length of 300 μm, and a width of 30 μm. The gap between the two flexible fingers 33 is 200 μm.

[0028] The microgripper is positioned in the magnetic field having a density of the magnetic flux of 0.5 Wb/m² so that the orientation of the magnetic flux is parallel to the length of the flexible fingers 33. Electric current is supplied to the coil layer 37 through the electrode layers 41 and the connection layers 39 by an external power source. The relation between an applied voltage and a displacement of the flexible fingers 33 was observed. With a voltage application of ±0.5 V, the flexible fingers 33 displaced as much as ±50 μm. Thus, a large amount of displacement of the flexible fingers 33 is obtained by a relatively low voltage, and a high degree of freedom with respect to the dimensions of a sample can be achieved.

[0029] Each flexible finger 33 has a coil layer 37, and electric power is separately supplied to the respective flexible fingers 33. In other words, each of the flexible fingers 33 can be powered and moved independently. Even if a sample object is located offset from the center line between the pair of flexible fingers 33, the microgripper can reliably nip the sample object by separately driving at least one of the flexible fingers 33 in its maximum bending range and by simply moving the flexible fingers 33 along its longitudinal direction.

[0030] FIG. 3 schematically illustrates several examples of movements of the flexible fingers 33, showing how the flexible fingers 33 move to nip a different size and position of sample object in connection with directions of electric current supplied to the coil layers 37. In this figure, magnetic flux acts from the top to the bottom of the drawing paper.

[0031] A direction of electric current flowing through the coil layer 37 is indicated by an arrow within the flexible finger 33 which is seen from the outer side of the microgripper. In FIG. 3(a), electric current is supplied to the coil layers 37 of the two flexible fingers 33 in the clockwise direction, and both the flexible fingers 33 bend inward to nip a relatively small sample object S.

[0032] In FIG. 3(b), electric current is supplied to the coil layers 37 in the counterclockwise direction, and both the flexible fingers 33 bend outward. A relatively large sample object S is positioned between the two flexible fingers 33 which have bent outward.

[0033] In FIG. 3(c), electric current is supplied to the two coil layers 37 in opposite directions, and the flexible fingers 33 bend to the left. A relatively small sample object is positioned between the two flexible fingers 33 which haven bent to the left.

[0034] In FIG. 3(d), electric current is supplied to the coil layer 37 in the opposite directions, but in the reversed directions from electric current supplied in FIG. 3(c). The two flexible fingers 33 bend to the right, nipping a sample object therebetween.

[0035] FIG. 4 shows another example of manufacturing process of the microgripper. First, a single-crystalline silicon substrate 53 with a thickness of 380 μm and a surface orientation of 100 is prepared as the substrate material to form a gripper body 31 and flexible fingers 33.

[0036] A silicon oxide film 55 having a thickness of 0.4 μm is formed on either surface of the single-crystalline silicon substrate 53 through thermal oxidation as shown in FIG. 4(a). A portion of the silicon oxide film 55 is removed by lithography, and the single-crystalline silicon substrate 53 is anisotropically etched using KOH solution to form trenches 57 on either side of the substrate 53.

[0037] Then, a silicon oxide film 59 is again formed up to 0.1 μm on the entire area of the silicon oxide film 55 through thermal oxidation, as shown in FIG. 4(b). In FIG. 4(c), the silicon oxide films 59 and 55 are patterned into a rectangular shape by lithography to define the outline of the flexible fingers 33.

[0038] Then, a conductive film 61 is formed of aluminum through vacuum evaporation so as to cover the entire area of the silicon oxide film 59 and the substrate 53 (FIG. 4(d)). The conductive film 61 is patterned to form coil layers 37, connection layers 39 and electrode layers 41 (FIG. 4(e)).

[0039] Finally, in FIG. 4(f), an unnecessary portion is removed from the single-crystalline silicon substrate 53 by etching to complete the microgripper shown in FIG. 1.

[0040] The flexible finger 33 of the resultant microgripper has a thickness of 0.5 µm, a length of 600 µm, and a width of 30 µm. The gap between the two flexible fingers 33 is 380 µm.

[0041] The microgripper is positioned in the magnetic field having a density of the magnetic flux of 0.7 Wb/m$^2$ so that the orientation of the magnetic flux is parallel to the length of the flexible fingers 33. Electric current is supplied to the coil layer 37 through the electrode layers 41 and the connection layers 39 by an external power source. The relation between an applied voltage and a displacement of the flexible fingers 33 was observed. With a voltage application of ±0.3 V, the flexible fingers 33 displaced as much as about ±60 µm.

[0042] FIG. 5 shows still another example of manufacturing process of the microgripper. First, a single-crystalline silicon substrate 63 having a thickness of 400 µm and a surface orientation of 100 is prepared as the substrate material to form a gripper body 31 and flexible fingers 33.

[0043] A polyimide film 65 having a thickness of 3 µm is formed on either surface of the single-crystalline silicon substrate 63. As shown in FIG. 5(a), a portion of the polyimide film 65 is removed by lithography, and the single-crystalline silicon substrate 63 is anisotropically etched using KOH solution to form a trench 67 on either side of the substrate 53.

[0044] Then, a polyimide film 69 is again formed up to 0.5 µm on the entire area of the polyimide 65, as shown in FIG. 5(b). In FIG. 5(c), the polyimide films 69 and 65 are patterned into a rectangular shape by lithography to define the outline of the flexible fingers 33.

[0045] Then, a conductive film 71 is formed of aluminum through vacuum evaporation so as to cover the entire area of the silicon oxide film 69 and the substrate 63 (FIG. 5(d)). The conductive film 71 is patterned to form coil layers 37, connection layers 39 and electrode layers 41 (FIG. 5(e)).

[0046] Finally, in FIG. 5(f), an unnecessary portion is removed from the single-crystalline silicon substrate 63 by etching to complete the microgripper shown in FIG. 1.

[0047] The flexible fingers 33 of the resultant microgripper has a thickness of 3.5 µm, a length of 600 µm, and a width of 351 µm. The gap between the two flexible fingers 33 is 400 µm.

[0048] The microgripper is positioned in the magnetic field having a density of the magnetic flux of 0.4 Wb/m$^2$ so that the orientation of the magnetic flux is parallel to the length of the flexible fingers 33. Electric current is supplied to the coil layer 37 through the electrode layers 41 and the connection layers 39 by an external power source. The relation between an applied voltage and a displacement of the flexible fingers 33 was observed. With a voltage application of ±0.5 V, the flexible fingers 33 displaced as much as about ±100 µm.

[0049] FIG. 6 illustrates another example of a microgripper according to the invention. The end portion 73 of the flexible fingers 33 is tapered so as to have a triangular shape. This arrangement makes it easy to pass a nipped sample to another microgripper.

[0050] FIG. 7 illustrates still another example of a microgripper according to the invention. First and second coil layers 37a and 37b are formed on the outer surface of each flexible finger 33.

[0051] The first coil layer 37a is formed along the periphery of the rectangular flexible finger 33, and the second coil layer 37b is formed inside the first coil layer 37a with a predetermined interval from the first coil layer 37a. The projecting end of the second coil layer 37b is positioned in the middle of the flexible finger 33 along the longitudinal direction.

[0052] Connection layers 39a and 39b are formed on the gripper body 31, to which both ends of the first and second coil layers 37a and 37b are connected, respectively. Two pairs of electrode layers 41a and 41b are also formed on the gripper body 31 with a predetermined space therebetween, to which the connection layers 39a and 39b are connected, respectively.

[0053] A plurality of protrusions 77, which function as nippers 77, are formed on the tip of the inner surface of the flexible finger 33. The microgripper shown in FIG. 7 is manufactured by the same process as one of the processes shown in FIGS. 2, 4 and 5, except for the fact that the first and second coil layers 37a, 37b, the two pairs of connection layers 39a, 39b, and the two pairs of electrode layers 41a, 41b are formed when patterning the conductive film 51, 61, or 71, instead of forming a single coil layer 37.

[0054] This microgripper has the same effect and advantage as those described in connection with the previous examples. In addition, because the first and second coil layers 37a and 37b are formed on each of the flexible fingers 33, the flexible fingers 33 can be bent more freely with more complicated movement.

[0055] Thus, even if a sample object S is not located exactly in the middle of the two flexible fingers 33, the microgripper can nip the sample S by moving the flexible fingers 33 to the left and right, and along the longitudinal direction of the flexible fingers 33. Even after the sample object is nipped by the flexible fingers 33, the sample object can be moved to the left or right, or along the longitudinal direction of the flexible fingers 33 without moving the microgripper itself simply by controlling electric supply to the coil layers 37a and 37b.

[0056] In other words, the nipped sample S can be reliably moved to the left or right by utilizing a bend of the flexible fingers 33, without moving the microgripper itself. FIG. 8 schematically illustrates several examples showing how the flexible fingers 33 move to nip a sample object, together with directions of electric current supplied to the first and second coil layers 37a and 37b. Magnetic flux acts from the top to the bottom of the drawing paper.

[0057] Directions of electric current flowing through the coil layers 37a and 37b are indicated by arrows within the flexible finger 33 which is seen from the outer side of the microgripper.

[0058] In FIG. 8(a), electric current is supplied to the first coil layer 37a in the clockwise direction, and the front half of the flexible finger 33 bends inward. Meanwhile, electric current is supplied to the second coil layer 37b in the counterclockwise direction, and the back half of the flexible finger 33 bends outward. A sample S is nipped by the tips of the flexible fingers 33.

[0059] In FIG. 8(b), the voltage applied to the electrode layers 41a, 41b (and to the coil layers 37a, 37b) is reduced from the state shown in FIG. 8(a) to decrease the bending amount of the flexible fingers 33, thereby moving the nipped sample frontward.

[0060] FIG. 9 illustrates still another example of the microgripper, in which three coil layers 37a, 37b and 37c are formed in one flexible finger 33a. The flexible finger 33a having the three coil layers 37a, 37b and 37c bends inward in three steps at the projecting ends of the respective coil layers 37a, 37b and 37c.

[0061] FIG. 10 illustrates still another example of the microgripper, in which rigidity reinforcing layers 79 are formed from the conductive film mentioned above so as to extend along both sides of the flexible finger 33 from the projecting end of the second coil layer 37b (shown in FIG. 7) to the vicinity of the projecting end of the first coil layer 37a.

[0062] The rigidity reinforcing layers 79 are formed during the patterning of the conductive film for the purpose of making the rigidity of the front half and the back half of the flexible finger 33 substantially equal. In this arrangement, displacement of the flexible fingers 33 can be estimated more reliably and predictably.

[0063] In the embodiments described above, nippers 35, 77 are formed as one or more protrusions on the tip of the flexible finger 33. However, the present invention is not limited to this example, and it is obvious that the nippers may be formed as indentations.

[0064] In the embodiments, the coil layer 37 is formed from a conductive film made of gold, copper, or aluminum; however, the coil layer 37 may be made of, for example, $YBa_2$, $Cu_3$, $Ox$, or superconductive material containing $YBa_2$, $Cu_3$ or $Ox$. If this is the case, heat generation from the coil layer 37 is reduced, and consequently, thermal deformation of the flexible fingers 33 can be efficiently prevented.

[0065] Although, in the embodiment, one or more coil layers 37 are formed on both the flexible fingers 33, the coil layer(s) 37 may be formed on one of the flexible layers 33.

[0066]

[Advantage of the Invention]

A large amount of displacement (bend) of the flexible fingers can be achieved by relatively low voltage application. Each of the flexible fingers 33 can be independently moved in a wide range by simply controlling the state of electric supply, the microgripper can have a high degree of freedom with respect to types and dimensions of a sample object to nip.

[0067] A coil layer 37 is formed in each of the flexible fingers 33, and electric supply to the coil layer 37 is separately controlled. Accordingly, even if a sample object S is not located exactly in the middle of the two flexible fingers 33, the microgripper can nip the sample S by moving the flexible fingers 33 to the left and right, and along the longitudinal direction of the flexible fingers 33.

[0068] If two or more coil layers 37 are formed in at least one flexible finger 33, even a nipped sample object can be moved to the left or right, or along the longitudinal direction of the flexible fingers 33 without moving the microgripper itself simply by separately controlling electric supply to the coil layers 37.

[0069] If the flexible fingers are formed of inorganic material, such as a silicon nitride film, the manufacturing process becomes very easy. On the other hand, if organic material, such as a polyimide film, is used to form the flexible fingers, then the amount of bend in the flexible fingers increases.

[0070] If the coil layer is formed of superconductive material, thermal deformation of the flexible fingers can be efficiently prevented.

[BRIEF DESCRIPTION OF THE DRAWINGS]

FIG. 1 is a perspective view of a microgripper according to an embodiment of the invention.

FIG. 2 shows an example of a manufacturing process of the microgripper shown in FIG. 1.

FIG. 3 shows movements of the flexible fingers of the microgripper shown in FIG. 1 in connection with the states of electric supply.

FIG. 4 shows another example of a manufacturing process of the microgripper shown in FIG. 1.

FIG. 5 shows still another example of a manufacturing process of the microgripper shown in FIG. 1.

FIG. 6 is a perspective view of a microgripper according to another embodiment of the invention.

FIG. 7 is a perspective view of a microgripper according to still another embodiment of the invention.

FIG. 8 shows movements of the flexible fingers of the microgripper shown in FIG. 7 in connection with the states of electric supply.

FIG. 9 shows another example of movement of modified flexible fingers of a microgripper.

FIG. 10 is a plan view of a microgripper according to still another embodiment of the invention.

FIG. 11 is a cross-sectional view of a conventional microgripper.

FIG. 12 is a cross-sectional view of a another conventional microgripper.

[List of the Elements]

31 ... gripper body

33 ... flexible finger 35, 77 ... nippers 37, 37a, 37b, 37c ... coil layer

What is claimed is:

1. An apparatus for measuring a stress-versus-strain characteristic of a microscopic specimen, the apparatus comprising:

(a) a microgripper comprising at least one finger movable a certain amount upon application of a corresponding certain amount of electrical energy to the finger, each such finger being operable to move sufficiently to contact the specimen without stressing the specimen and to move sufficiently relative to the specimen to apply a stress to the specimen, each such movement being a function of the amount of electrical energy applied to the finger;

(b) means for determining any strain d of the specimen occurring as a result of application of a stress to the specimen using the microgripper, compared to when no stress is being applied to the specimen;

(c) means for measuring the amount of electrical energy $V_O$ applied to each finger before applying the stress to the specimen and the amount of electrical energy $V_F$ applied to each finger during application of the stress to the specimen using the microgripper; and (d) means for calculating, from $V_O$, $V_F$, and d, a stress-versus-strain characteristic of the specimen.

2. The apparatus of claim 1, wherein said means for determining the strain comprises a microscope operable to produce an enlarged image of the specimen, the microscope including a scale for measuring dimensions of the specimen as viewed in the enlarged image.

3. The apparatus of claim 2, further comprising an imaging device operable to capture the enlarged image of the specimen, and a display operable to display the captured image.

4. The apparatus of claim 1, wherein the finger is operable to apply a compressive stress to the specimen situated between the finger and a stationary object.

5. The apparatus of claim 4, wherein the finger is operable to apply a tensile stress to a stationary specimen.

6. The apparatus of claim 1, wherein the microgripper comprises a pair of opposing fingers, the fingers being cooperative to provide a compression stress to the specimen situated between the fingers.

7. The apparatus of claim 1, wherein the finger is operable to reflect light, and said means for measuring strain of the specimen comprises (i) a light projector operable to project a beam of light and cause the beam of light to be incident on the finger in a manner by which the light reflects from the finger; (ii) a light sensor situated relative to the finger so as to receive light reflected from the finger, the light sensor being operable to sense changes in trajectory of the reflected light as a function of finger position; and (iii) means for calculating, from a change in finger position as sensed by the light sensor after applying the stress to the specimen compared with before applying the stress, a value of d.

8. The apparatus of claim 7, wherein said means for calculating a value of d includes means for making the following calculation:

$$\delta/L1 = \tan(2\alpha)$$

wherein $\delta$ is the displacement of light on the light sensor, L1 is a predetermined distance from the point at which light reflects from the finger to the light sensor, and $\alpha$ is the flex angle of the finger.

9. The apparatus of claim 1, wherein said means for measuring strain of the specimen comprises (i) a microscope operable to produce an enlarged optical image of the specimen; (ii) an imaging device operable to capture the optical image of the specimen and produce a screen image of specimen; and (iii) means for processing the screen image obtained while applying a stress to the specimen compared to the screen image obtained before applying the stress to the specimen so as to determine an amount of dimensional change experienced by the specimen while a stress is being applied compared to before the stress was applied.

10. The apparatus of claim 9, wherein said means for processing the screen image comprises means for converting the screen image into pixels, wherein the amount of dimensional change experienced by the specimen while a stress is being applied compared to before the stress was applied is determined based upon a change in illumination status of the pixels.

11. The apparatus of claim 1, further comprising a microscope and microscope stage, the stage being operable to move the specimen to a position adjacent a finger of the microgripper prior to application of a stress to the specimen.

12. The apparatus of claim 11, further comprising a manipulator to which the microgripper is attached, the manipulator being operable to move the microgripper relative to the specimen.

13. The apparatus of claim 1, wherein the finger has a spring constant $k_s$, a bimorph drive coefficient $k_B$, and a Lorentz force coefficient $k_L$, the finger comprising a microcoil having an electrical resistance R.

14. The apparatus of claim 13, wherein said means for measuring the strain d comprises means for performing the calculation:

$$d = k_B(V_F^2/R) + k_L(V_F/R).$$

15. The apparatus of claim 14, wherein said means for calculating a stress-versus-strain characteristic is operable to perform the calculation:

$$F_g = k_s[(k_B/R)V_F^2 + (k_L/R)V_F - (K_B/R)V_0^2 - (k_L/R)V_0] - k_s \cdot d$$

wherein $F_g$ is the force applied to the specimen by the finger whenever the finger is applying the stress to the specimen.

16. A method for measuring a stress-versus-strain characteristic of a microscopic specimen, the method comprising the steps:

(a) disposing the specimen relative to a finger of a microgripper operable to move the finger a distance corresponding to an amount of electrical energy supplied to the microgripper;

(b) measuring an amount of electrical energy $V_0$ supplied to the microgripper when the finger is contacting the specimen but not applying a stress to the specimen;

(c) supplying an amount of electrical energy $V_F$ to the microgripper to urge movement of the finger relative to the specimen sufficient to cause the finger to apply a stress to the specimen;

(d) measuring $V_F$; and (e) measuring a dimensional change d imparted to the specimen as a result of the stress applied to the specimen.

17. The method of claim 16, wherein steps (c), (d), and (e) are performed simultaneously.

18. The method of claim 17, wherein step (e) comprises performing the calculation:

$$d = k_B(V_F^2/R)$$

wherein $k_B$ is the bimorph drive coefficient of the finger, $K_L$ is the Lorentz force coefficient of the finger, and R is the electrical resistance of the finger.

19. The method of claim 16, further comprising the step of calculating, from $V_0$, $V_F$, and d, a value of the stress applied to the specimen.

20. The method of claim 19, wherein the step of calculating a value of the stress comprises performing the following calculation:

$$F_g = k_s[(k_B/R)V_F^2 + (k_L/R)V_F - (k_B/R)V_0^2 -$$

$$k_L/R)V_0] - k_s \cdot d$$

wherein $k_s$ is a spring constant of the finger, and $F_g$ is a force applied to the specimen in step (c).

* * * * *

UNITED STATES PATENT AND TRADEMARK OFFICE
CERTIFICATE OF CORRECTION

PATENT NO. : 5,723,793

DATED : March 3, 1998

INVENTORS : Suzuki et al.

It is certified that error appears in the above-identified patent and that said Letters Patent is hereby corrected as shown below:

Column 2, line 44, "compressire" should be --compressive--.

Column 2, line 46, "compressire" should be --compressive--.

Column 13, line 45, "351 $\mu$m" should be --35 $\mu$m--.

Column 16, line 60, "compressire" should be --compressive--.

Column 18, line 35, "$d=k_B(V_F^2/R)$" should be --$d = k_B(V_F^2/R) + k_L(V_F/R)$--.

Column 18, lines 48-50, "$F_g=k_s[(k_B/R)V_F^2+(k_L/R)V_F-(k_B/R)V_0^2-k_L/R)V_0]-k_s\cdot d$" should be -- $F_g = k_s[(k_B/R)V_F^2 + (k_L/R)V_F - (k_B/R)V_0^2 - (k_L/R)V_0] - k_s\cdot d$ --.

Signed and Sealed this

Sixteenth Day of February, 1999

Attest:

*Attesting Officer*

*Acting Commissioner of Patents and Trademarks*